United States Patent
Brandt et al.

(10) Patent No.: US 12,408,710 B2
(45) Date of Patent: Sep. 9, 2025

(54) FLEXIBLE COOLING GARMENT SYSTEM

(71) Applicant: Nike, Inc., Beaverton, OR (US)

(72) Inventors: Baron C. Brandt, Portland, OR (US); Kevin C. Sze, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 240 days.

(21) Appl. No.: 17/873,949

(22) Filed: Jul. 26, 2022

(65) Prior Publication Data

US 2022/0354194 A1 Nov. 10, 2022

Related U.S. Application Data

(62) Division of application No. 16/429,577, filed on Jun. 3, 2019, now Pat. No. 11,425,944.

(60) Provisional application No. 62/724,972, filed on Aug. 30, 2018.

(51) Int. Cl.
*A41D 13/005* (2006.01)
*A41D 1/04* (2006.01)

(52) U.S. Cl.
CPC ........... *A41D 13/0053* (2013.01); *A41D 1/04* (2013.01); *A41D 13/0058* (2013.01)

(58) Field of Classification Search
CPC ............ A41D 13/0518; A41D 13/0575; A41D 13/0568; A41D 13/0053; A41D 13/0058; A41D 1/04; A61F 2007/0018; A61F 2007/0233; A61F 2007/0019; A61F 2007/0022; A61F 2007/0024; A61F 2007/0225; A61F 2007/023; A61F 2007/0234; A61F 2007/0238; A61F 2007/108; A61F 7/10; A61F 2007/0273; F25D 2400/26

See application file for complete search history.

(56) References Cited

U.S. PATENT DOCUMENTS

| | | | |
|---|---|---|---|
| 695,629 A | 3/1902 | Shipley | |
| 2,391,535 A | 12/1945 | Joseph | |
| 2,691,171 A * | 10/1954 | Masi | A41D 27/20 2/247 |
| 3,074,250 A | 1/1963 | Everett | |

(Continued)

FOREIGN PATENT DOCUMENTS

| CA | 2810287 A1 | 9/2014 |
|---|---|---|
| CN | 2824609 Y | 10/2006 |

(Continued)

OTHER PUBLICATIONS

International Preliminary Report on Patentability received for PCT Patent Application No. PCT/US2021/048348, mailed on Mar. 23, 2023, 8 pages.

(Continued)

*Primary Examiner* — Heather Mangine
(74) *Attorney, Agent, or Firm* — Shook, Hardy & Bacon L.L.P.

(57) ABSTRACT

Aspects herein are directed to a cooling garment. The cooling garment can include a vest configured to be worn by a wearer. One or more pockets on the vest may be configured to receive one or more icepacks. The one or more pockets may include a stretch material on a front portion of the one or more pockets. The one or more pockets can further include a non-stretch material on a back portion of the one or more pockets.

14 Claims, 9 Drawing Sheets

(56) References Cited

U.S. PATENT DOCUMENTS

| | | | |
|---|---|---|---|
| 3,476,102 A | 11/1969 | Sarnoff | |
| 3,761,962 A | 10/1973 | Myers | |
| 3,802,215 A | 4/1974 | Rowe | |
| 3,950,789 A | 4/1976 | Konz et al. | |
| 4,032,681 A | 6/1977 | Jonnes | |
| 4,033,354 A | 7/1977 | De | |
| 4,243,041 A | 1/1981 | Paul | |
| 4,583,247 A | 4/1986 | Fingerhut et al. | |
| 4,601,067 A | 7/1986 | Buonassissi | |
| D292,140 S | 10/1987 | Cahill et al. | |
| 4,856,294 A | 8/1989 | Scaringe et al. | |
| 5,033,118 A | 7/1991 | Lincoln | |
| 5,038,779 A | 8/1991 | Barry et al. | |
| 5,060,314 A | 10/1991 | Lewis | |
| 5,072,455 A | 12/1991 | St | |
| 5,086,629 A | 2/1992 | Dibrell | |
| 5,129,391 A | 7/1992 | Brodsky et al. | |
| 5,146,625 A | 9/1992 | Steele et al. | |
| 5,157,788 A | 10/1992 | Schultz | |
| 5,215,080 A | 6/1993 | Thomas et al. | |
| 5,235,975 A | 8/1993 | Gang et al. | |
| 5,265,782 A | 11/1993 | Mcnamara | |
| 5,290,218 A | 3/1994 | Kilbey | |
| 5,302,806 A | 4/1994 | Simmons et al. | |
| 5,415,222 A | 5/1995 | Colvin et al. | |
| 5,484,448 A | 1/1996 | Steele et al. | |
| 5,495,622 A | 3/1996 | Kaufman | |
| 5,524,293 A * | 6/1996 | Kung | A41D 13/0058 2/102 |
| 5,606,746 A | 3/1997 | Shelton et al. | |
| 5,652,967 A | 8/1997 | Hsu | |
| 5,692,238 A | 12/1997 | Watson, Jr. | |
| 5,776,177 A * | 7/1998 | MacWhinnie | A61M 1/064 128/890 |
| 5,864,880 A * | 2/1999 | Adam | A45F 3/20 2/108 |
| 5,978,961 A | 11/1999 | Barker | |
| 5,993,480 A | 11/1999 | Burrows | |
| 6,009,560 A | 1/2000 | Mckenney et al. | |
| 6,105,382 A | 8/2000 | Reason | |
| 6,185,742 B1 | 2/2001 | Doherty | |
| 6,189,149 B1 | 2/2001 | Allen | |
| 6,241,711 B1 | 6/2001 | Weissberg et al. | |
| 6,241,771 B1 * | 6/2001 | Gresser | A61F 2/4455 606/77 |
| 6,320,095 B1 | 11/2001 | Wall | |
| 6,421,839 B1 | 7/2002 | Vo et al. | |
| 6,451,046 B1 | 9/2002 | Leo et al. | |
| 6,931,875 B1 | 8/2005 | Allen et al. | |
| 6,955,999 B1 | 10/2005 | Boye | |
| 7,309,275 B1 | 12/2007 | Morales | |
| 7,437,774 B2 | 10/2008 | Baron et al. | |
| 7,490,358 B1 | 2/2009 | Beck | |
| D599,529 S | 9/2009 | Simpson | |
| 7,739,748 B2 | 6/2010 | Nilforushan et al. | |
| 8,099,794 B2 | 1/2012 | Carstens | |
| 8,105,371 B1 | 1/2012 | Giocondo, Jr. | |
| 8,220,074 B2 | 7/2012 | Sutker | |
| 8,434,163 B1 | 5/2013 | Nudo | |
| 8,449,588 B2 | 5/2013 | Horn | |
| 8,479,322 B2 | 7/2013 | Blackford et al. | |
| 8,793,815 B1 | 8/2014 | Kelley-mozsy | |
| 8,918,919 B2 | 12/2014 | Scholz | |
| 9,032,550 B2 | 5/2015 | Lambertz | |
| 9,167,856 B1 | 10/2015 | Pacific | |
| 9,332,792 B2 | 5/2016 | Harber | |
| 9,717,287 B2 | 8/2017 | Dibernardo et al. | |
| 10,179,075 B1 | 1/2019 | Hickling | |
| 10,264,831 B1 | 4/2019 | Hemker | |
| 10,544,502 B2 | 1/2020 | Conolly et al. | |
| 10,674,778 B2 | 6/2020 | Coza et al. | |
| 11,019,865 B2 | 6/2021 | Pezzimenti et al. | |
| 11,425,944 B2 * | 8/2022 | Brandt | A41D 13/0058 |
| 2001/0037076 A1 | 11/2001 | Shelton | |
| 2002/0016984 A1 * | 2/2002 | Poholski | A41D 13/0058 607/108 |
| 2003/0023291 A1 * | 1/2003 | Hanner | A61F 7/02 607/108 |
| 2003/0079277 A1 | 5/2003 | Gillen et al. | |
| 2004/0199983 A1 | 10/2004 | Gillen et al. | |
| 2004/0244412 A1 | 12/2004 | Trinh et al. | |
| 2004/0248487 A1 | 12/2004 | Yasumitsu | |
| 2005/0070980 A1 * | 3/2005 | Noonan | A61F 7/02 607/108 |
| 2005/0101220 A1 | 5/2005 | Jackson | |
| 2005/0107856 A1 * | 5/2005 | Gammons | A61F 7/02 607/104 |
| 2005/0223465 A1 * | 10/2005 | Williams | A41D 13/005 2/102 |
| 2006/0036304 A1 | 2/2006 | Cordani et al. | |
| 2006/0073324 A1 | 4/2006 | Otto et al. | |
| 2006/0085888 A1 | 4/2006 | Webb | |
| 2006/0156449 A1 | 7/2006 | Shows | |
| 2007/0150033 A1 * | 6/2007 | Johnson | A61F 7/106 607/114 |
| 2007/0299489 A1 | 12/2007 | Francis et al. | |
| 2008/0066484 A1 | 3/2008 | Blackstone | |
| 2009/0038046 A1 * | 2/2009 | Moore | A41F 9/025 2/67 |
| 2009/0070913 A1 | 3/2009 | Park | |
| 2009/0138064 A1 | 5/2009 | Horn | |
| 2010/0057173 A1 * | 3/2010 | Leavitt | A61F 7/10 607/114 |
| 2010/0083421 A1 | 4/2010 | Cho | |
| 2012/0047622 A1 | 3/2012 | Van | |
| 2012/0078147 A1 | 3/2012 | Ogulnick et al. | |
| 2012/0142253 A1 | 6/2012 | Javaid et al. | |
| 2012/0167288 A1 | 7/2012 | Chen et al. | |
| 2012/0210488 A1 | 8/2012 | Blakely et al. | |
| 2012/0260395 A1 * | 10/2012 | Maynard | A41D 13/0015 2/84 |
| 2012/0260396 A1 | 10/2012 | Mordecai | |
| 2012/0285191 A1 | 11/2012 | Gallaher | |
| 2013/0116762 A1 | 5/2013 | Lai | |
| 2013/0204332 A1 | 8/2013 | Amalfi | |
| 2013/0276218 A1 | 10/2013 | Parisi et al. | |
| 2014/0025145 A1 | 1/2014 | Kirkman | |
| 2014/0157484 A1 | 6/2014 | Ezell | |
| 2014/0188199 A1 * | 7/2014 | Enderby | A61M 1/062 607/108 |
| 2014/0245527 A1 | 9/2014 | Douglas et al. | |
| 2014/0277301 A1 * | 9/2014 | Varga | A61F 7/02 607/104 |
| 2015/0065923 A1 | 3/2015 | Schaede | |
| 2015/0150716 A1 * | 6/2015 | Whitely | A61F 7/02 607/104 |
| 2015/0153140 A1 | 6/2015 | Crye et al. | |
| 2015/0313301 A1 | 11/2015 | Shineman et al. | |
| 2015/0359665 A1 | 12/2015 | Vasconcellos | |
| 2015/0366281 A1 | 12/2015 | Miller et al. | |
| 2015/0374043 A1 | 12/2015 | Dahl | |
| 2015/0374045 A1 | 12/2015 | Codner et al. | |
| 2016/0021941 A1 | 1/2016 | Jen | |
| 2016/0135517 A1 | 5/2016 | Silverberg | |
| 2016/0227847 A1 * | 8/2016 | Gibbons | A41D 27/28 |
| 2016/0366954 A1 | 12/2016 | Barkshire et al. | |
| 2017/0013890 A1 | 1/2017 | Byrne | |
| 2017/0055602 A1 | 3/2017 | Abraham | |
| 2017/0065005 A1 * | 3/2017 | Nordstrom | A41D 27/10 |
| 2017/0182733 A1 * | 6/2017 | Orologio | A41D 31/065 |
| 2017/0202696 A1 | 7/2017 | Sandwith | |
| 2017/0203191 A1 | 7/2017 | Lemieux et al. | |
| 2017/0231299 A1 | 8/2017 | Feterman | |
| 2017/0296380 A1 | 10/2017 | Barger et al. | |
| 2017/0296381 A1 | 10/2017 | Fox et al. | |
| 2017/0297664 A1 | 10/2017 | Berry | |
| 2017/0320286 A1 | 11/2017 | Carlson | |
| 2017/0340027 A1 | 11/2017 | Montoya et al. | |
| 2017/0340037 A1 * | 11/2017 | Bailey | A41D 13/0015 |
| 2017/0354266 A1 | 12/2017 | Nordentoft | |
| 2017/0354530 A1 | 12/2017 | Shagdar et al. | |
| 2017/0360598 A1 | 12/2017 | Mcgregor | |

(56) References Cited

U.S. PATENT DOCUMENTS

| | | | |
|---|---|---|---|
| 2018/0049489 A1* | 2/2018 | Noll | A41D 3/00 |
| 2018/0049913 A1 | 2/2018 | Spears et al. | |
| 2018/0098879 A1 | 4/2018 | Smith et al. | |
| 2018/0192720 A1* | 7/2018 | Blackford | B32B 5/24 |
| 2018/0243486 A1* | 8/2018 | Blackwell | A61M 1/67 |
| 2018/0283827 A1 | 10/2018 | 't Hart et al. | |
| 2018/0317573 A1 | 11/2018 | Devito | |
| 2018/0343936 A1 | 12/2018 | Morgan et al. | |
| 2018/0343944 A1 | 12/2018 | Morgan | |
| 2018/0360133 A1 | 12/2018 | Blackwell | |
| 2018/0364011 A1 | 12/2018 | Blakeley | |
| 2019/0008676 A1 | 1/2019 | Kilbey | |
| 2019/0075868 A1 | 3/2019 | Morgan | |
| 2019/0116902 A1 | 4/2019 | Blackford et al. | |
| 2019/0187345 A1 | 6/2019 | Gold et al. | |
| 2019/0216191 A1 | 7/2019 | Botha et al. | |
| 2019/0289936 A1 | 9/2019 | Hourani | |
| 2020/0054080 A1 | 2/2020 | Luo | |
| 2020/0068964 A1 | 3/2020 | Brandt et al. | |
| 2020/0209442 A1 | 7/2020 | Gold et al. | |
| 2020/0335005 A1 | 10/2020 | Green et al. | |
| 2020/0375283 A1 | 12/2020 | Check et al. | |
| 2020/0397072 A1 | 12/2020 | Arnold et al. | |
| 2021/0059325 A1 | 3/2021 | Yazawa | |
| 2021/0186136 A1 | 6/2021 | Romano | |
| 2021/0186749 A1 | 6/2021 | Kates | |
| 2021/0361473 A1 | 11/2021 | Crowe | |

FOREIGN PATENT DOCUMENTS

| | | |
|---|---|---|
| CN | 2910155 Y | 6/2007 |
| CN | 202665783 U | 1/2013 |
| CN | 203988614 U | 12/2014 |
| CN | 207733695 U | 8/2018 |
| EP | 0917888 A2 | 5/1999 |
| JP | 2007-51381 A | 3/2007 |
| JP | 2011-218006 A | 11/2011 |
| JP | 2011-218007 A | 11/2011 |
| JP | 3184824 U | 6/2013 |
| JP | 3187781 U | 11/2013 |
| JP | 2019-197378 A | 11/2019 |
| RU | 2062590 C1 | 6/1996 |
| WO | 94/23677 A3 | 10/1994 |
| WO | 2006/128420 A1 | 12/2006 |
| WO | 2009/056296 A1 | 5/2009 |
| WO | 2011/056035 A2 | 5/2011 |

OTHER PUBLICATIONS

Notice of Allowance received for U.S. Appl. No. 17/014,704, mailed on Feb. 15, 2023, 8 pages.
Intention to Grant received for European Patent Application No. 19734989.7, mailed on Aug. 16, 2022, 7 pages.
Adjustable Zipper Cooling Vest with (5-12) Small Kool Max® Packs, Polar Products, polarproducts.com SKU: KMVZ-KM, Available Online at:<nttps://web.archive.org/web/20160825212732/http://www.polarproducts.com/polarshop/pc/Adjustable-Zipper-Cooling-Vest-with-5-12-Small-Kool-Max-Packs-p32.htm>, Apr. 24, 2018, 20 pages.
Chillybuddy Canine Cooling Jacket, Clean Run, 1995-2020, 1 page.
Classic Cool Vest—Safety Blue with Protect Pack, Glacier Tek glaciertek.com, SKU:RCVC15SB-A, Available Online at:<nttps://web.archive.org/web/20180424193929/https:/lwww.glaciertek.com/classic-cool-vest-safely-blue-with-comfortpack/>, Apr. 24, 2018, 2 pages.
Cooling Vest Kit, Shu Bee, shubee.com, SKU#: D SB CV KIT-C Available Online at:<hllps://web.archive.org/web/20180424203301/hllp:/lwww.shubee.com/cooling-vest-kit-1504.html>, Apr. 24, 2018, 2 pages.
Mesh Cooling Vest, All Safe Industries®, allsafeindustries.com Item#: AMORV, MFG: Kappler Available Online at:<hllps://web.archive.org/web/20180424194 7 44/https://www.allsafeindustries.com/store/p/5914-Mesh-Cooling-Vesl.asp,>, Apr. 24, 2018, 3 pages.
PCCS Phase Cool Light—Lightweight Economy Cooling Vest, EnviroSafety™ envirosafetyproducts.com SKU: OCCPCL Available Online at:<hllps://web.archive.org/web/20111116124529/hllp://w ww.envirosafetyproducts.com/pees-phase-cool-light-lightweight-economy-cooling-vest.html>, Nov. 16, 2011, 2 pages.
Phase Change Cool Vests—PCM, Arctic Heat Body Cooling Vests, coolingvests.com Available Online at:<hllps://web.archive.org/web/20180424193314/https://www.coolingvests.com/collections/industrial-cooling-vests>, Apr. 24, 2018, 1 page.
See why UnderCool is the #1 cooling vest around, Therm Apparel, thermapparel.net Available Online at:<hllps://web.archive.org/web/20 180501042659/https://www.thermapparel.net/cooler-than-you/>, May 1, 2018, 5 pages.
Silver Shade Mesh: Cools Everything Under the Sun, 2016, 1 page.
Solar Reflective Clothing, IPS Innovative Products & Systems, Available online at: <http://www.ips-innovations.com/solar_reflective_clothing.htm>, Accessed on Feb. 15, 2015, 1 page.
Stacool Under Vest, StaCool Vest™, stacoolvesl.com Available Online at:<nttps://web.archive.org/web/20140510235414/hllp://www.stacoolvesl.com/stacoolunder-vesl/>, May 10, 2014, 3 pages.
Extended European Search Report received for European Patent Application No. 22202386.3, mailed on Jan. 30, 2023, 6 pages.
Final Office Action received for U.S. Appl. No. 17/014,704, mailed on Oct. 14, 2022, 24 pages.
Invitation to Pay Additional Fee received for PCT Patent Application No. PCT/US2019/036495, mailed on Sep. 18, 2019, 13 pages.

\* cited by examiner

FLEXIBLE COOLING GARMENT SYSTEM

CROSS-REFERENCE TO RELATED APPLICATIONS

This U.S. application Ser. No. 17/873,949 and entitled "Flexible Cooling Garment System," filed Jul. 26, 2022 is a divisional application of U.S. application Ser. No. 16/429,577, filed Jun. 3, 2019, and entitled "Flexible Cooling Garment System"; now U.S. Pat. No. 11,425,944, issued on Aug. 30, 2022, which claims the benefit of priority to U.S. Prov. App. No. 62/724,972, filed Aug. 30, 2018, and entitled "Flexible Cooling Garment System." The entireties of the aforementioned applications are incorporated by reference herein.

TECHNICAL FIELD

Aspects herein relate to a flexible cooling garment system that is configured to cool a wearer.

BACKGROUND

Traditional cooling garments (e.g., cooling vests) may not adequately support the weight or shape of articles that are coupled with the cooling vests, such as icepacks. Moreover, traditional cooling garments and icepacks may be rigid or otherwise not flexible such that they do not adequately conform to the wearer's body or cause discomfort during wearer activity.

DESCRIPTION OF THE DRAWINGS

Examples of aspects herein are described in detail below with reference to the attached drawings figures, wherein.

DETAILED DESCRIPTION

Figure 1:
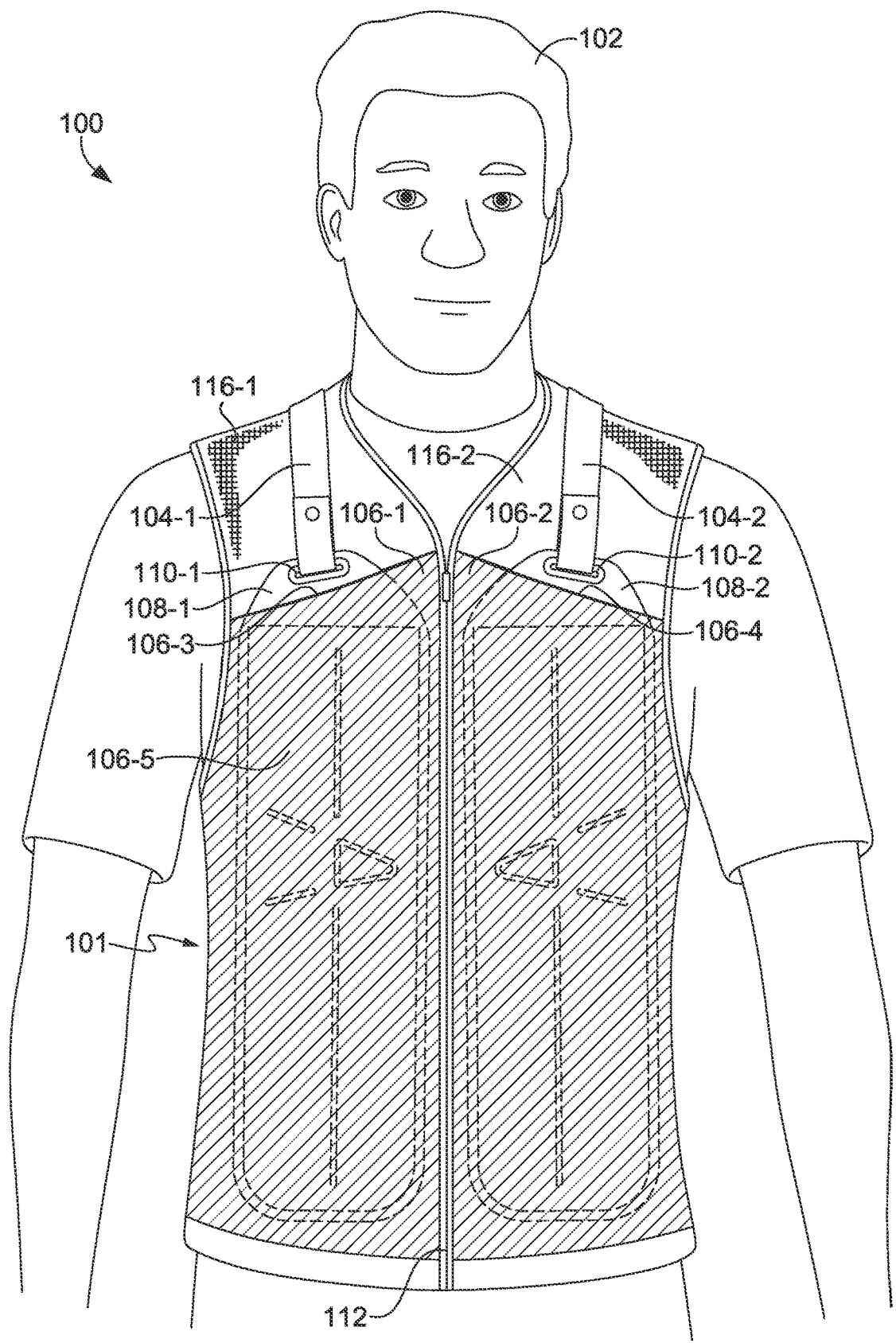
FIG. 1 illustrates a front view of an example cooling vest system being worn by a wearer, in accordance with aspects herein.

The subject matter of the present invention is described with specificity herein to meet statutory requirements. However, the description itself is not intended to limit the scope of this disclosure. Rather, the inventors have contemplated that the claimed or disclosed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

At a high level, certain aspects herein relate to a flexible cooling garment system configured to cool a wearer before, during, and/or after an activity (e.g., a workout). In one aspect, the cooling garment system can include a vest configured to be worn by a wearer and one or more pockets on the vest configured to receive one or more icepacks. These pockets may be formed from a first inner layer of material which may comprise a non-stretch material and a second outer layer of material which may comprise a stretch material. The stretch material of the second outer layer of the pocket may help secure the one or more icepacks to the wearer's torso, as the stretching of the garment may allow an icepack to fully expand to its capacity while additionally cause increased pressure against a surface area of the icepack due to the elastic properties of the stretch material. Additionally, the non-stretch material of the first inner layer of the one or more pockets can help support the weight of the icepacks such that the icepacks do not sag or otherwise move outside of intended contact points on the wearer's body.

In still further aspects, a system can include one or more icepacks that include at least a first aperture configured to receive a first end of at least one shoulder strap. The system can further include a garment that includes one or more pockets configured to receive the one or more icepacks. The shoulder strap may be disposed over a shoulder region of the garment and may include a first end that is configured to pass through the first aperture of the one or more icepacks. The shoulder strap can further help secure the one or more icepacks to a wearer's torso and support the icepack's weight and shape. The shoulder strap can help secure the one or more icepacks to the wearer's torso by keeping an icepack in an upright extended position, as opposed to a strapless system, which may result in a folding or compression of the icepack due to gravitational and other movement forces especially as the ice within the icepack begins melting. In some aspects, a particular end of the shoulder strap extends downward when the garment is in an as-worn configuration and fastens to a superior portion of the icepack, which allows the icepack to maintain its expanded shape, as gravitational forces pull downward on the icepack, while the shoulder strap keeps the icepack in an upright position. The shoulder strap can also help prevent the icepack from shifting or bouncing during wear and various activities while wearing, such as working out or engaging in a sport. In this way, the icepacks can maintain continuous contact with the wearer, as opposed to sporadic contact that may happen without a shoulder strap mechanism.

In yet other aspects, an icepack configured for use with a cooling garment can include at least one flexion area. These flexion areas may correspond to one or more points or areas at which a first front portion of the icepack and a first back portion of the icepack are affixed to each other, such that the one or more points or areas are not filled with a filler substance (e.g., water). The icepack can further include one or more second apertures disposed adjacently to the at least one flexion area. These apertures may extend from a second front portion of the icepack through a second back portion of the icepack. The flexion areas and apertures on the icepack can allow the icepack to more closely conform to a wearer's chest or other body part and allow for a generally unabated range of motion. For example, various flexion areas on an icepack may effectively act as joints or axis points about which the rest of the corresponding icepack portions can axially rotate or move. Accordingly, for example, the icepack can more closely conform to the contours of the wearer's body because the flexion areas may bend at areas where the body changes size or shape. In another example, the apertures and flexion areas can also act as hinges or points about which the rest of the icepack can move during particular wearer movements. Without these apertures and/or flexion areas, the icepack is generally prevented from bending or folding according to wearer movement, which may cause discomfort or strain during movement. The apertures can decrease the surface area of the icepack and act as a movement point such that when a wearer moves, there is less rigidity and the icepack can conform more to the contours of the wearer.

Positional and range of motion terms as used herein such as "inner," "outer," "medial," "lateral," "upper," "lower," "superior," "inferior," "anterior," "posterior," "flexion," "extension," "abduction," "adduction," and the like are to be given their common meaning with respect to the cooling garment being worn as intended and as shown and described herein by a hypothetical wearer standing in an upright position (i.e., standing in anatomical position). Still further, the phrase "configured to contact," or other similar phrases used when describing different portions of the garment in relation to a wearer refer to a support garment appropriately sized for the particular wearer. Terms such as "fastened" or "secured" as used herein generally refer to attachment methodologies between two or more elements that generally maintain the elements in a fixed relationship with respect to one another. Terms such as "adjustably secured" as used herein refer to attachment methodologies that allow at least one element, such as a strap, to be adjusted (e.g., shortened or lengthened) in relation to another element, such as an upper portion of an icepack surface.

The term "stretch material" as used herein refers to textiles or materials formed using elastomeric yarns. Elastomeric yarns may generally provide a maximum stretch greater than about 200% under load prior to returning to its non-stretched state when the load is removed, and some elastomeric yarns provide a maximum stretch of about 400%. Examples of elastomeric yarn types include spandex, LYCRA®, rubber, and the like. Moreover, examples of stretch materials or textiles may include stretch woven materials, stretch knit materials, stretch non-woven materials, and the like. The term "non-stretch material" as used herein refers to textiles or materials that are formed using non-elastomeric yarns that generally do not stretch over a threshold amount (e.g., cotton, silk, polyester, conventional denim, and/or other non-elastic polymers). To describe this differently, non-stretch materials have a lower stretching capacity than stretch materials.

The term "cooling garment" or "garment" as used herein may mean an upper-body garment (e.g., a vest, a shirt, a jacket, a coat, a support garment, and the like), a lower-body garment (e.g., shorts, pants, and the like), or a combination upper-body garment and lower-body garment (e.g., a unitard, overall, and the like).

Turning now to FIG. 1, a front perspective view of an example cooling garment system 100 being worn by a wearer 102 is illustrated in accordance with aspects herein. Although the cooling garment system 100 is depicted as including a vest 101, it is understood that the cooling garment system 100 may alternatively or additionally include any suitable cooling garment, such as a shirt, jacket, and/or other wearable article. The vest 101 includes pockets 106, which includes the pocket 106-1, pocket 106-2, the inlet opening 106-3, the inlet opening 106-4, and the outer layer 106-5. The pockets 106-1 and 106-2 are located on an anterior or front portion of the vest 101, and is disposed over a front torso and chest portion of the wearer 102. The pockets 106-1 and 106-2 are each respectively configured to receive icepacks 108-1 and 108-2 (collectively referred to herein as the "icepacks 108"). The pockets 106-1 and 106-2 may each respectively include the inlet opening 106-3 and 106-4 at an upper portion of the pockets 106-1 and 106-2 such that respective icepacks 108-1 and 108-2 can be inserted into the pockets 106-1 and 106-2. In some aspects, the inferior or bottom of the pockets 106-1 and 106-2 may not include an inlet, such that the weight of the icepacks 108 can be supported. Although the cooling garment system 100 depicts the two icepacks 108-1 and 108-2 and the two pockets 106-1 and 106-2, it is understood that this quantity is representative only and that there may be any suitable quantity. For example, in some aspects, the cooling garment system 100 may comprise a single pocket and a single corresponding icepack or more than two pockets and corresponding icepacks.

The cooling garment system 100 further includes an optional slider mechanism 112, which is disposed in between the pockets 106-1 and 106-2 and may form, in some aspects, an inner or medial edge of the pockets 106-1 and 106-2. The slider mechanism 112 may include a tape that extends along a longitudinal or vertical length of the pockets 106-1 and 106-2. The slider mechanism 112 includes a slider pull configured to reversibly open and close the slider mechanism 112 and, accordingly, open and close the vest 101 such that the wearer 102 can put on or remove the vest 101. Although the cooling garment system 100 includes the slider mechanism 112 as a fastening mechanism, it is understood that any suitable fastening mechanism can alternatively or additionally be used to secure or put on the vest 101. For example, instead of the wearer 102 zipping up the vest 101 via the slider mechanism 112, the wearer 102 in various aspects secures the vest 101 via one or more buttons, snaps, or hook-and-loop fasteners.

As mentioned, the cooling garment system 100 further includes the icepacks 108-1 and 108-2, each of which respectively include apertures 110-1 and 110-2 at the superior or upper portions of the icepacks 108. These apertures (collectively described herein as "apertures 110") and the rest of the upper portions of the icepacks 108 are illustrated as being exposed or not covered by a portion of the pockets 106 or vest 101. This may make it easier for the wearer 102 to remove and/or place the icepacks 108 to/from the inlet opening 106-3 and inlet opening 106-4 of the pockets 106-1 and 106-2 and/or make it easier for the wearer 102 to fasten shoulder straps 104-1 and 104-2 to the icepacks 108 via the apertures 110. The shoulder straps 104-1 and 104-2 (collectively referred to herein as the shoulder straps 104) are each configured to fasten or be secured to the icepacks 108 via placing respective ends through the apertures 110, as described in more detail below. The shoulder straps 104 are oriented, at least in part, horizontally or transversely over a shoulder region of the vest 101 (e.g., 116-1) or wearer 102 and longitudinally oriented over the anterior portion of the vest 101 or wearer 102 to attach to the upper portion of the icepacks 108. In various aspects, the icepacks 108 can include various flexion areas and additional apertures, as described in more detail below.

The vest 101 includes inner layer portions 116-1 and 116-2 (collectively described herein as the "inner layer 116"). The inner layer 116 is positioned adjacent to a front or face portion (i.e., the outer layer 106-5) of the pockets 106 such that opposing surfaces of the inner layer 116 and the outer layer 106-5 of the pockets 106 are positioned adjacent to each other. In particular aspects, the pockets 106 are formed as a space between the inner layer 116 and the outer layer 106-5, and the outer layer 106-5 may only be present in certain portions of the vest 101 such as where the pockets 106 are located. In this way, the icepacks 108-1 and 108-2 are disposed between the inner layer 116 and outer layer 106-5. The inner layer 116 may comprise the inner-most layer of the vest 101 such that it is positioned adjacent to a body surface of the wearer 102 (e.g., either a skin surface or a surface of the wearer 102 covered by, for instance, a base layer).

The inner layer portion 116-1 may abut and be positioned beneath the shoulder strap 104-1. In some aspects, the shoulder straps 104 are sewn or otherwise permanently fixed to the inner layer 116. In other aspects, the shoulder straps 104 are stand-alone articles, such that they are not sewn or permanently attached to the inner layer 116 and, instead, are removably attached to the inner layer 116 using, for example, hook-and-loop fasteners, snaps, buttons, and the like. Although the vest 101 is shown without sleeves, in some aspects the inner layer 116-1 may extend to form short or long sleeves (e.g., sleeves of a long sleeved T-shirt) such that a portion of the wearer's 102 arm is covered (e.g., the length of a person's entire arm down to a wrist portion of the arm). The vest 101 further includes a neck opening inner layer portion 116-2 of the inner layer 116 that is configured to be placed over the wearer 102's head in order to wear the vest 101. In some aspects, the portions (not shown) of the inner layer 116 that are positioned beneath the icepacks 108 represent the back side or posterior part of the pockets 106. The inner layer 116 or any part of the cooling garment system 100 can be made from any suitable material, such as knitted mesh, woven material, nylon, cotton, polyester, silk, etc. In various aspects, the inner layer 116 or posterior portion of the pockets 106 is formed from a non-stretch material, such as non-stretch woven, a non-stretch knit, a non-stretch nonwoven, and the like. In various aspects, the outer layer 106-5 is formed from a stretch material including a stretch woven, a stretch knit, a stretch nonwoven, and the like.

Figure 2:
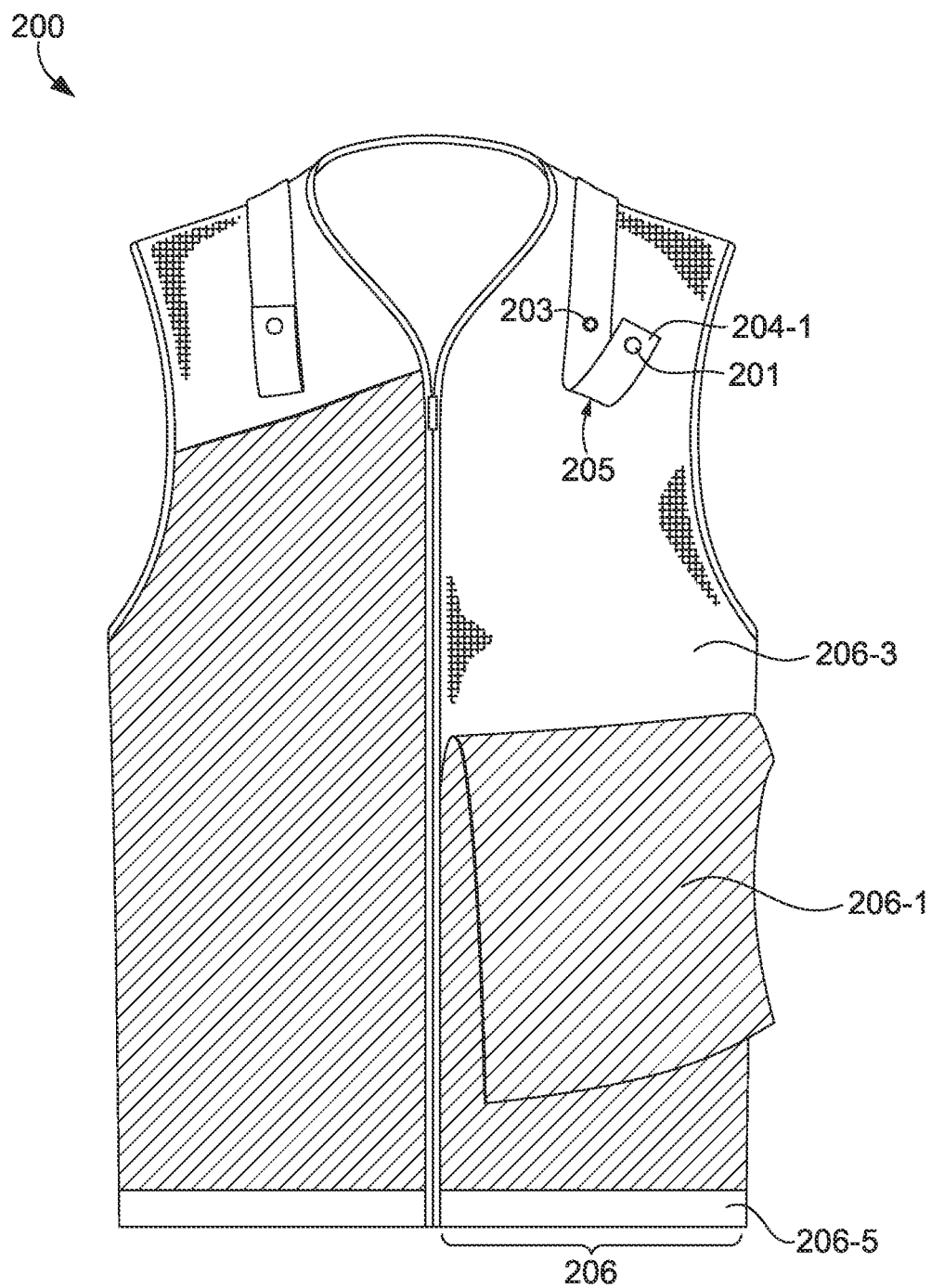
FIG. 2 illustrates a front view of a shoulder strap and a front view of a pocket of a cooling garment with a second outer layer of the pocket partially detached to better illustrate the pocket, in accordance with aspects herein.

FIG. 2 illustrates a shoulder strap 204-1 and a view of a pocket 206 (representing both the first inner layer 206-3, the second outer layer 206-1, and the lower margin 206-5) of a cooling garment 200 with a portion of a second outer layer 206-1 of the pocket 206 partially detached to better illustrate the pocket 206. In some embodiments, the cooling garment 200 represents the vest 101 of FIG. 1 and vice versa. For example, in some aspects, the pocket 206 represents the pocket 106-1 (and/or 106-2) of FIG. 1 and vice versa. In some aspects, the first inner layer 206-3 represents the inner layer 116-1 and/or 116-2 of FIG. 1 and vice versa. Likewise, in some aspects, the second outer layer 206-1 represents the outer layer 106-5 of FIG. 1 and vice versa. In example aspects, the first inner layer 206-3 may form remaining portions of the cooling garment 200. An inner-facing surface of the second outer layer 206-1 is positioned adjacent to an outer-facing surface of the first inner layer 206-3 such that the second outer layer 206-1 forms at least a portion of an exterior surface of the cooling garment 200 and is at least partially viewable while a wearer is wearing the associated cooling garment 200. In aspects, the first inner layer 206-3 may comprise an interior (or body-facing) layer of the cooling garment 200. In some aspects, the second outer layer 206-1 is or includes a stretch material (e.g., a stretch-woven material) and the first inner layer 206-3 is or includes a non-stretch material.

By structuring the pocket 206 such that the second outer layer 206-1 of the pocket 206 is formed from a stretch material and the first inner layer 206-3 of the pocket 206 is formed from a non-stretch material, the pocket 206 is configured to both support the weight of an icepack and help conform the icepack closer to the body of a wearer. Because the first inner layer 206-3 includes the non-stretch material, it supports an icepack in its inserted or upright position such that the icepack does not sag or orient downward due to gravitational forces. In some example aspects, a lower margin 206-5 of the second outer layer 206-1 also includes non-stretch material in order to further prevent sagging or drooping of the icepack. Because the second outer layer 206-1 generally comprises the stretch material, the inserted icepack may conform more to a wearer than portions with a non-stretch material because the stretch material may keep an icepack in its extended or upright form (e.g., the icepack does not sag, deform, bend, and the like) and keep continuous pressure on the icepack and thus a wearer. For instance, a wearer may have to exert an initial tension on the second outer layer 206-1 in order to insert the icepack in the pocket 206. However, because of the elastic nature of stretch material, the stretch material may engage in the elastic process of returning to its original shape when the icepack is fully positioned in the pocket 206. Therefore, there may be greater pressure against the body of the wearer due to elastic forces and the icepack may not fold or compress because of these elastic forces countering gravitational forces. In some aspects, the stretch material allows the wearer to more easily place an icepack in the pocket inlet than an otherwise rigid non-stretch material because of the ability of the pocket to stretch.

The shoulder strap 204-1 includes at least a first end that contains, for instance, a male end 201 of a connecting element and a portion that includes a female end 203 of the connecting element. In some aspects, the first end of the shoulder strap 204-1 is configured to pass through the aperture 110-2 of the icepack 108-2 and the male end 201 can be snapped or secured into the female end 203 such that a portion of the icepack 108-2 is secured to the shoulder strap 204-1 at loop portion 205. In this manner, when the male end 201 and the female end 203 are coupled, the shoulder strap 204-1 forms a loop and the icepack 108-2 can then extend from the newly formed loop portion 205 by way of the aperture 110-2. Although FIG. 2 illustrates that the shoulder strap 204-1 includes a snap mechanism to help fasten the icepacks to the cooling garment 200, in other aspects, the shoulder strap 204-1 can include other fasteners, such as hook-and-loop fasteners, buttons, releasable adhesives, and the like. In some aspects, the shoulder strap 204-1 can be adjustably secured to the icepack 108-2 such that the wearer can loosen or tighten the shoulder strap 204-1.

Figure 3:
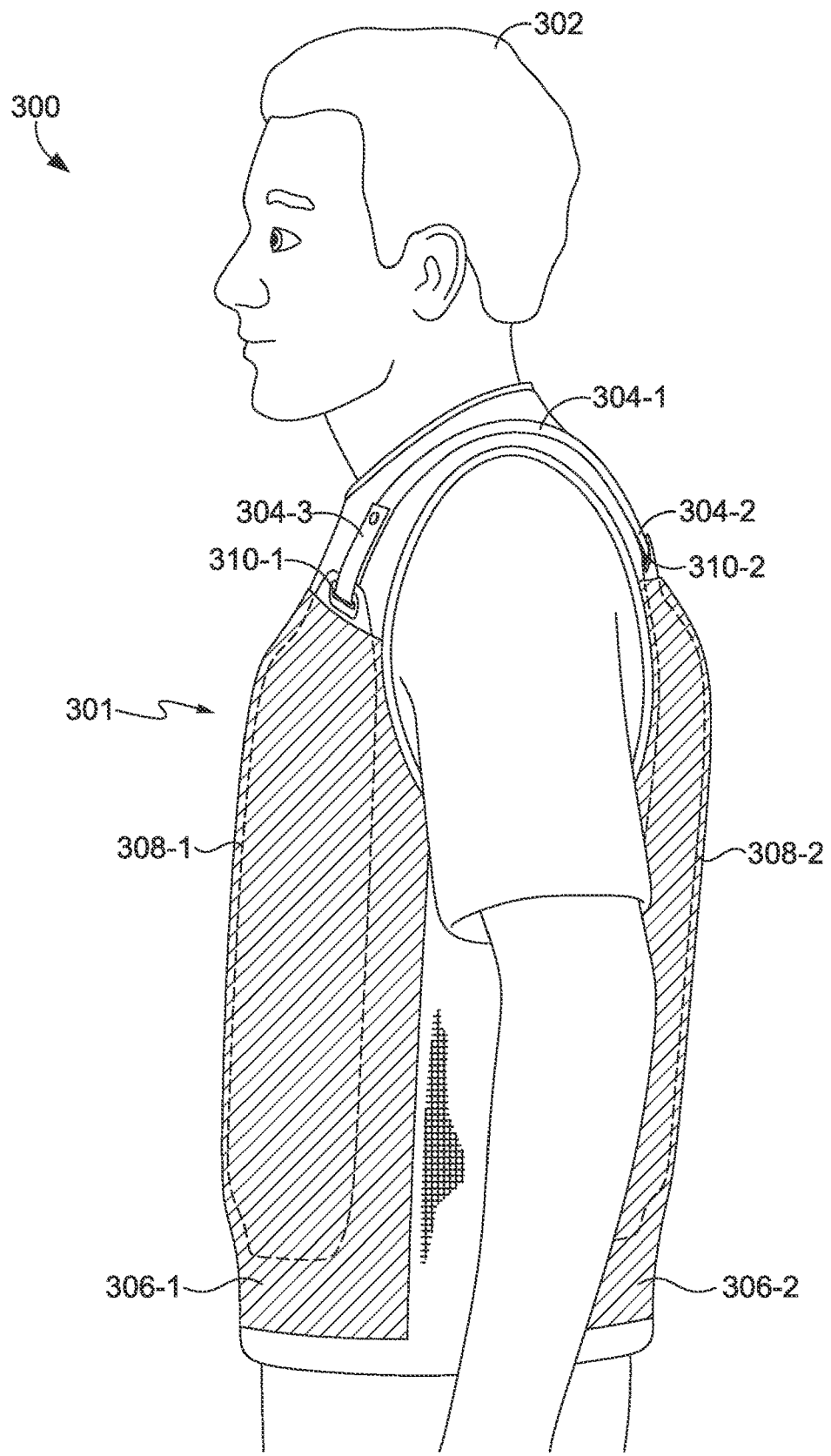
FIG. 3 illustrates a side view of a cooling garment system being worn by a wearer, in accordance with aspects herein.

FIG. 3 illustrates a side view of a cooling garment system 300 being worn by a wearer 302, in accordance with aspects of the present disclosure. In some aspects, the cooling garment system 300 represents a side view of the same cooling garment system 100 of FIG. 1 and/or cooling garment 200 of FIG. 2 and vice versa. In other aspects, however, the cooling garment system 100 may only have icepacks and pockets on the front portion of the cooling vest, such that there are no icepacks on a back portion, for example. The cooling garment system 300 includes a pocket 306-1 on a front portion of the garment 301 and a pocket 306-2 on a back portion of the garment 301, each of which are respectively configured to receive icepacks 308-1 and 308-2. In some aspects, there is a second pocket on the front portion and/or on the back portion (not visible because of the view).

FIG. 3 illustrates that shoulder strap 304-1 can help secure and hold both of the icepacks 308-1 and 308-2. A midsection of the shoulder strap 304-1 is disposed or oriented transversely over a shoulder region of the garment 301 or wearer 302. The shoulder strap 304-1 includes a second end 304-2 that is configured to be placed through an aperture 310-2 on the icepack 308-2 so as to be secured or fastened to the icepack 308-2 (e.g., in the manner described in FIG. 2). The shoulder strap 304-1 further includes a first end 304-3 that is configured to be placed through an aperture 310-1 on the icepack 308-1 so as to be secured or fastened to the icepack 308-1 (e.g., in the manner described in FIG. 2). Accordingly, the shoulder strap 304-1 in aspects is a continuous article that can help secure front and rear icepacks to the garment 301 so as to prevent the icepacks 308-1 and 308-2 from shifting or bouncing during wearer activities and help cool the chest and back of a wearer. Further, the shoulder strap 304-1 can help keep the icepacks 308 (representing both of the icepacks 308-2 and 308-2) in an upright position such that the icepacks 308 maintain their expanded shape (e.g., they do not fold, bend, twist, compress, deform, and the like) and maintain contact with more surface area of the wearer 302, as opposed to a strapless system, which may allow the icepacks 308 to fold or compress due to gravitational and other movement forces.

Figure 4:
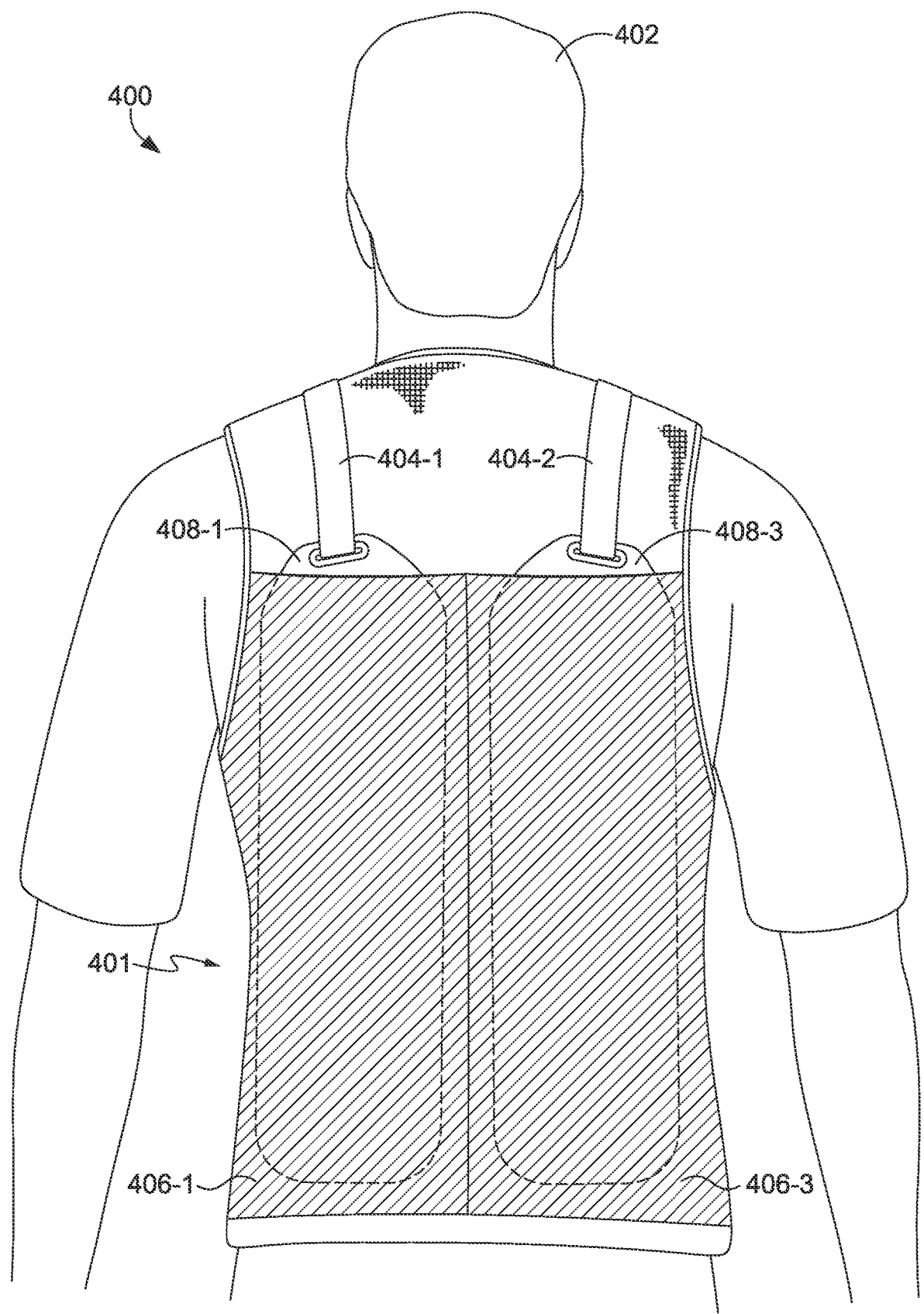
FIG. 4 illustrates a rear view of a cooling garment system being worn by a wearer, in accordance with aspects herein.

FIG. 4 illustrates a rear or posterior view of a cooling garment system 400 being worn by a wearer 402, in accordance with aspects herein. In some aspects, the cooling garment system 400 represents the rear view of the cooling garment system 100 of FIG. 1 (which shows the front view) and vice versa. Accordingly, for example the shoulder strap 404-1 can be the same shoulder strap 104-2 as illustrated in FIG. 1. Likewise, the shoulder strap 404-2 can be the same shoulder strap 104-1 of FIG. 1. In some aspects, the cooling garment system 400 represents the rear side of the cooling garment system 300 of FIG. 3 (which shows a side view) and/or the cooling garment 200 of FIG. 2 and vice versa.

The cooling garment system 400 includes pockets 406-1 and 406-3, each of which are configured to respectively receive icepacks 408-1 and 408-3. The shoulder straps 404-1 and 404-2 each include ends that are configured to be placed through respective apertures in the icepacks 408-1 and 408-3 in order to fasten or be secured to the icepacks 408-1 and 408-3. As described above, in some aspects cooling garment systems such as the cooling garment system 400 can include icepacks on a front side and a backside of the cooling garment system 400 or wearer 402 and the shoulder straps 404 may therefore be continuous articles that fasten to both front and backside icepacks. Accordingly, for example, a cooling vest 401 of the cooling garment system 400 can comprise the first shoulder strap (e.g., 404-2) (that includes first and second ends) and the second shoulder strap (e.g., 404-1) (that includes third and fourth ends). The first end of the first shoulder strap 404-2 may be configured to fasten to a first icepack (e.g., 108-1) on a front portion of the cooling vest 401. The second end of the first shoulder strap 404-2 can be additionally configured to fasten to a second icepack (e.g., 408-3) on a back portion of the cooling vest 401 (e.g., as illustrated in FIG. 2). The third end of the second shoulder strap 404-1 may be configured to fasten to a third icepack (e.g., 108-2) on the front portion of the cooling vest 401. The fourth end of the second shoulder strap 404-1 can be configured to fasten to a fourth icepack (e.g., 408-1) on the back portion of the cooling vest 401.

Figure 5:
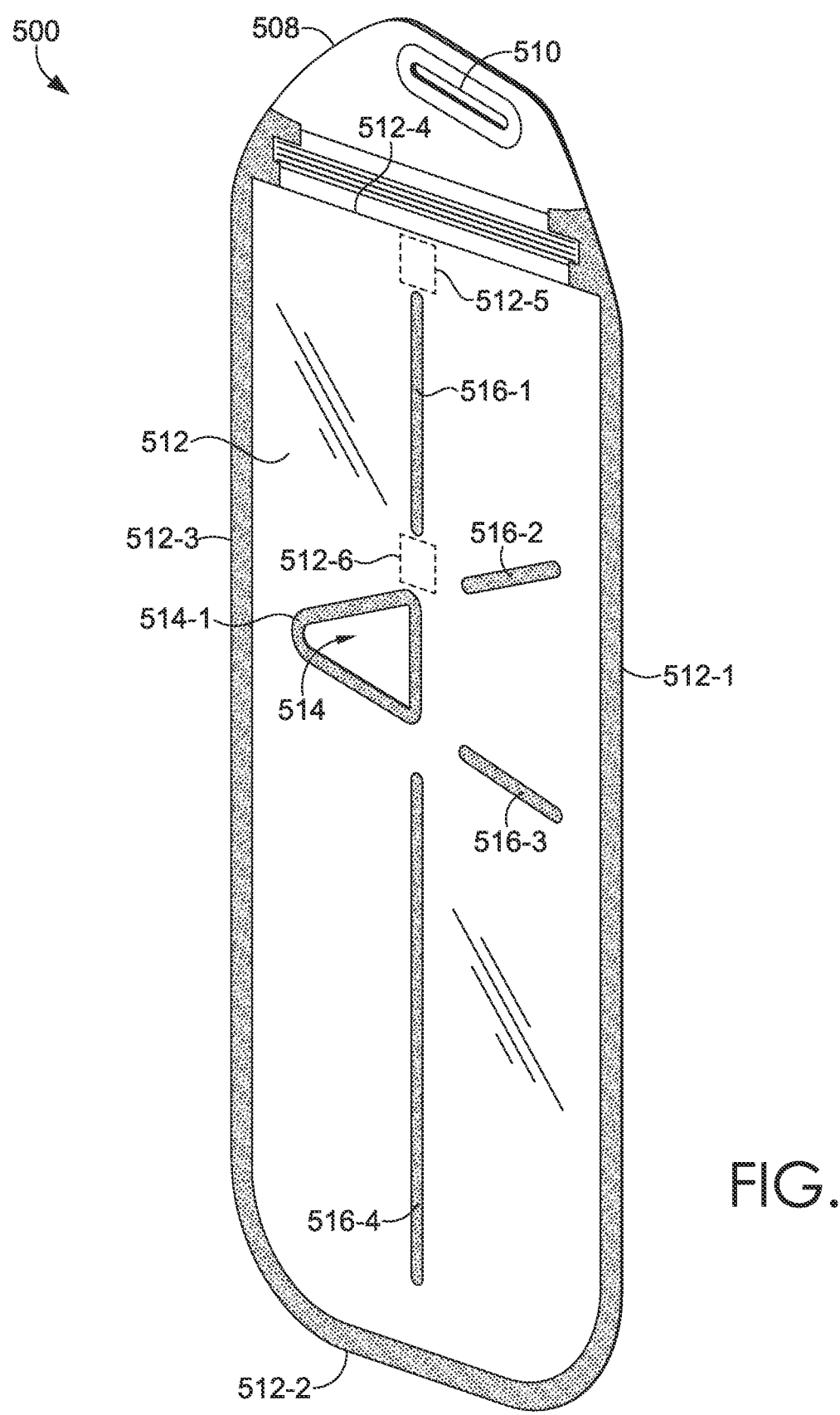
FIG. 5 is a schematic diagram illustrating a front perspective view of a first example icepack, in accordance with aspects herein.

FIG. 5 is a schematic diagram illustrating a front perspective view an icepack 500, in accordance with aspects herein. In some aspects, the icepack 500 represents any of the icepacks described with respect to the cooling garments systems of FIG. 1, FIG. 2, FIG. 3, and/or FIG. 4. The icepack 500 includes a top or upper portion 508, which includes a first aperture 510. The first aperture 510 is an open space, slit, or a through-hole that may be cylindrical in shape in order to receive a shoulder strap (e.g., the shoulder strap 104-1), such that the shoulder strap can fasten to the icepack 500, as described in FIG. 2, for example. In some aspects, the upper portion 508 is not configured to be filled with a liquid or substance, but is a panel that is configured to protrude or be exposed outside of a pocket inlet (e.g., the inlet opening 106-3) so that a wearer can easily place or remove the icepack 500 and/or easily fasten a shoulder strap to the icepack 500 via the first aperture 510. In some aspects, the upper portion 508 is or includes any suitable material, such as foam or any other polymer-based material. In some aspects, the upper portion 508 is made from a different material than a body 512 of the icepack 500.

The body 512 includes example flexion areas 516-1, 516-2, 516-3, and 516-4 (collectively referred to herein as the flexion areas 516) that surround or extend away from a second aperture 514. Although the icepack 500 illustrates a particular shape, orientation, quantity, and length of flexion areas, apertures, and icepacks themselves, it is understood that this is illustrative only and that any suitable shape, quantity, orientation, and length can exist. For example, in some aspects, the second aperture 514 represents a circular, rectangular, or square shape, as opposed to triangular as represented in FIG. 5. In another example, some or each of the flexion areas 516 are circular in shape, as opposed to cylindrical as represented in FIG. 5.

Each of the flexion areas 516 is an area at which a first respective front portion of the icepack 500 and a first respective back portion of the icepack 500 converge, bond, or affix to each other, as described in more detail below. Accordingly, the flexion areas 516-1, 516-2, 516-3, and 516-4 each have portions of the front and back of the icepack 500 that are bonded or affixed to each other. Because the front and back of the icepack 500 are affixed to each other at the flexion areas 516, these flexion areas 516 are unable to be filled with a filler substance, such as water. In one aspect, the flexion area 516-1 is cylindrical in shape and extends longitudinally from just inferior to an edge 512-4 (defined by a border between the upper portion 508 and the body 512) to just above the second aperture 514. The flexion areas 516-2 and 516-3 (also cylindrical shaped) extend obliquely or diagonally across the body 512 from a first side edge 512-1 of the body 512 to an area laterally adjacent to the second aperture 514. As illustrated, in an example aspect, these flexion areas 516-1 and 516-2 are oriented parallel or substantially parallel to respective edges or sides that form the second aperture 514. The flexion area 516-4 extends parallel with and is substantially aligned with the flexion area 516-1. The flexion area 516-4 extends longitudinally across a length of the body 512 from just inferior to the second aperture 514 to just above (or superior to) a bottom edge 512-2 of the body 512.

The second aperture 514 (or any apertures described with reference to an icepack body) is a hole or opening in an icepack body (e.g., the body 512) that extends from and through a front or face portion of the icepack 500 through a back or rear portion of the icepack 500. Accordingly, in these aspects, portions of the body 512 can form the borders of the entire space around the second aperture 514 such that there is open space that forms the second aperture 514. For example, a person can see through these apertures and some objects can pass through the apertures (e.g., a finger) in some aspects. FIG. 5 illustrates a triangular-shaped second aperture 514, with an apex 514-1. In some aspects, the apex 514-1 (defined as the vertex where two sides of equal length meet, opposite an unequal third side or base) of the triangular-shaped second aperture 514 is oriented toward a midline or medial portion of a cooling garment or wearer as illustrated in FIG. 1. In various aspects, the apertures (e.g., the second aperture 514) within the bodies of the icepacks are disposed adjacently or next to flexion areas, such as the flexion areas 516. The second aperture 514 is disposed near the center of the body 512 and in between the flexion areas 516-1 and 516-2. The second aperture 514 is further disposed adjacent to and medial of the flexion areas 516-2 and 516-3 when the icepack 500 is in an as-utilized configuration or worn as illustrated with respect to the icepack 108-1 of FIG. 1.

Each of the flexion areas 516 and the second aperture 514 allow more flexibility for cooling garments and wearers as well as allow the icepack 500 to more easily conform to a wearer, as described herein. For example, the flexion areas 516-1 and 516-4 extend across a portion of the longitudinal length of the body 512. Accordingly, if a wearer performs a horizontal adduction or horizontal abduction movement of the arm (e.g., to swing a bat), this may cause the body 512 to move or rotate in the direction of the movement, which may be substantially perpendicular to the length of the flexion areas 516. Accordingly, the flexion areas 516 may act as an effective axis point or line such that the body 512 can more freely move, thereby allowing more unabated range of motion by the wearer and greater contact of the icepack with the wearer, which can reduce discomfort or strain during movement. Likewise, the flexion areas 516 may act as effective joints, such that the body 512 of the icepack 500 can more easily conform to varied contours of a wearer's body, such as a chest region. In another example, if a wearer performs a flexion and extension movement of his or her trunk (e.g., a sit up motion), the second aperture 514 and the flexion areas 516-2 and 516-3 may act as effective axis areas so that a wearer can more easily flex and extend her trunk while at the same time allow for optimal contact between the body 512 of the icepack 500 and the wearer. Accordingly, in these movements, the second aperture 514 can bend or fold at the apex 514-1, and the body 512 can bend or fold at the flexion areas 516-2 and 516-3 during flexion and extension.

In various aspects, the body 512 is made from any suitable material. For example, the body 512 can be made from a thermoplastic-polyurethane material and/or other polymers such as low-density polyethylene, high-density polyethylene, polypropylene, and the like. The size of the icepack 500 can also include any suitable length, width, and thickness. For example, in some aspects, the width of the body 512 (defined by the distance along the edge 512-2 or the distance between the edge 512-1 and edge 512-3) is about 10 cm (e.g., plus or minus 5% of 10 cm). In some aspects, the length of the icepack 500 (defined by the distance along the edge 512-1 or the distance between edge 512-4 and 512-2 is from about 30 cm to about ~36 cm with the upper portion 508 (e.g., plus or minus 5% of 30 cm and 36 cm respectively)). In some aspects, the thickness of the body 512 is from about 2 cm to about 4 cm (e.g., plus or minus 5% of these values) without a fluid (e.g., water) or other filler substance.

In some aspects, the icepack 500 is formed from two separate layers that are adhered together at certain areas such as around the periphery (e.g., edges 512-1, 512-2, and 512-3), at the flexion areas 516 and/or around the perimeter edge of the second aperture 514.

Figure 6:
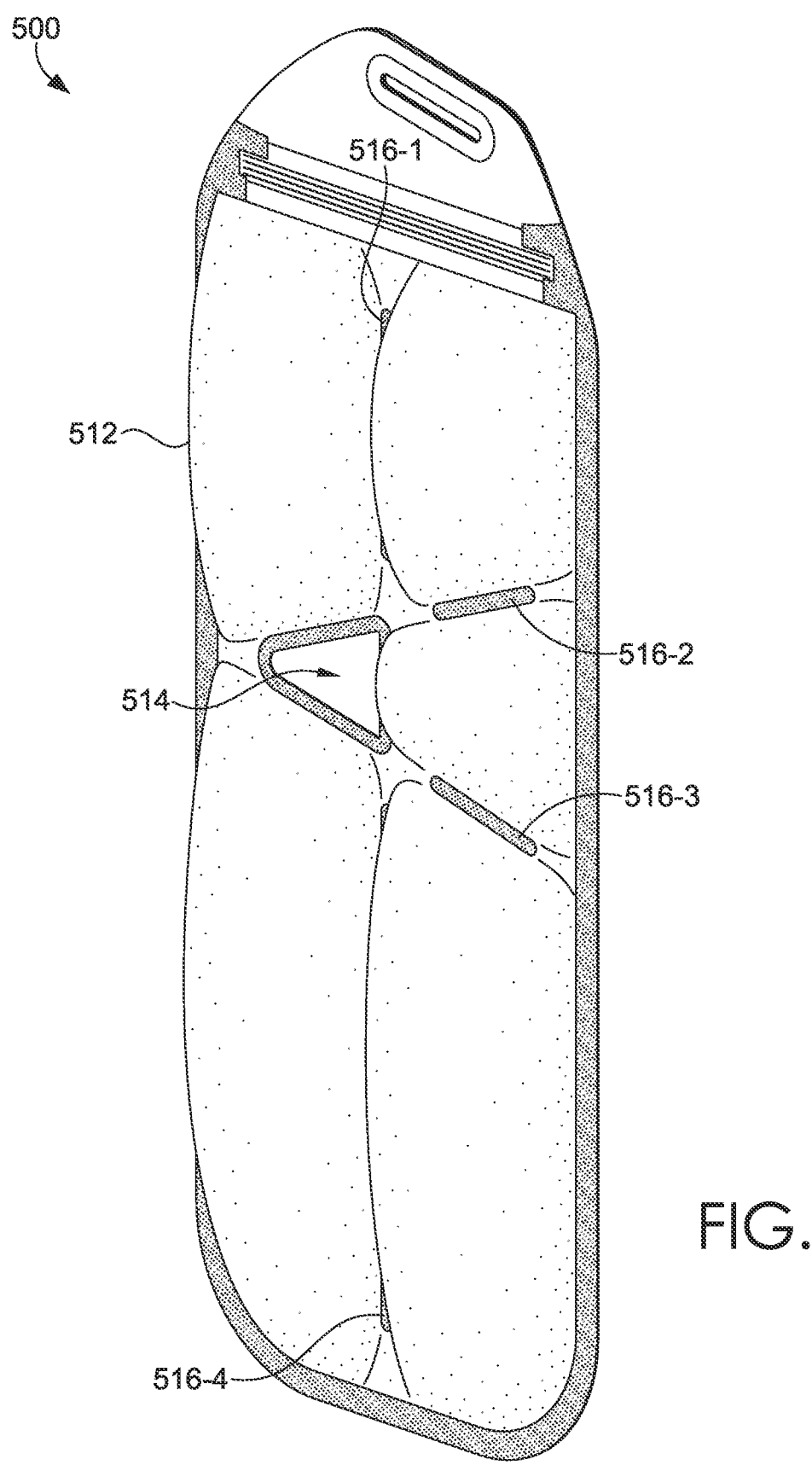
FIG. 6 illustrates a front perspective view of the icepack of FIG. 5, which is filled with a filler substance, in accordance with aspects herein.

As illustrated in FIG. 5, the flexion areas 516 do not extend to any of the edges of the body 512. Accordingly, fluid or other filler substances can surround each portion of some or each of the flexion areas 516, as described in more detail below. For example, a first edge 512-1 of the body 512 may extend across a longitudinal length of the body 512. A second edge 512-2 may extend along a horizontal width from the edge 512-1 to a portion (e.g., a corner) of the edge 512-3. The third edge 512-3 may be parallel with and extend the same distance as the edge 512-1. The fourth edge 512-4 may extend across a horizontal width and represent a line of demarcation between the upper portion 508 and the body 512 and further represent the top of the body 512. The edge 512-4 may be parallel with the edge 512-2. In an illustrative example, the flexion area 516-1 may extend longitudinally from just inferior the edge 512-4 to just above an edge of the second aperture 514. Accordingly, the flexion area 516-1 does not extend to the edge 512-4 and to the edge of the second aperture 514. Therefore, for example, the portions 512-5 and 512-6 can be filled with water or another substance because the flexion area 516-1 does not extend all the way to the edges. Therefore, the flexion area 516-1 can be surrounded entirely by a filler substance. In like manner, some or each of the other flexion areas may also not extend to nearby edges such that a filler substance can entirely surround each side of the flexion areas, as illustrated in FIG. 6. In other aspects, however, flexion areas can abut or extend to one or more edges of the body 512 of the icepack 500. Any and all aspects, and any variation thereof are contemplated as being within aspects herein.

FIG. 6 illustrates a front perspective view of the icepack 500 of FIG. 5, which is filled with a filler substance (e.g., gel, water, ice, etc.), in accordance with aspects herein. FIG. 6 illustrates what the icepack 500 can appear like when it is filled with a filler substance, such as water. Accordingly, the body 512 appears as bulging or expanded at each of the areas surrounding the flexion areas 516-1, 5-16-2, 516-3, 516-4 and the second aperture 514. The flexion areas 516 thus do not bulge or expand upon filling the icepack 500 with a filler substance because the flexion areas 516 are areas where the front and back layers of the icepack 500 are affixed, as described above. The second aperture 514 also does not bulge or expand upon filling the icepack 500 because the body 512 does not continue into this area. As such, water or other filler substances does not fill this space. FIG. 6 also illustrates that the flexion areas 516 and the second aperture 514 can be completely or entirely surrounded by a fluid or other filler substance, such that each area surrounding the second aperture 514 and flexion areas 516 is configured to bulge out or expand in response to filling the icepack 500 with a filler substance.

Figure 7:
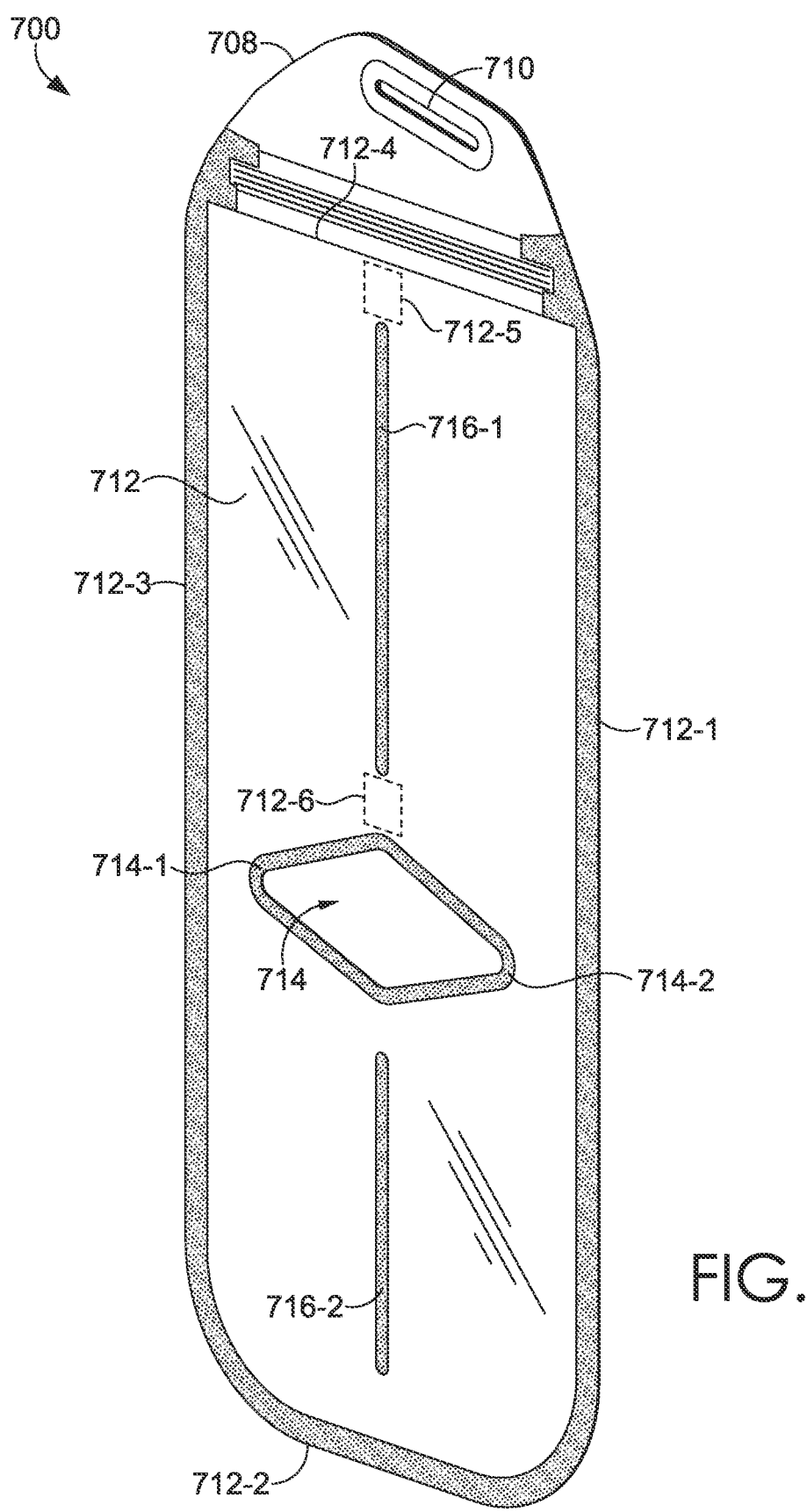
FIG. 7 is a schematic diagram illustrating a front perspective view of a second example icepack, in accordance with aspects herein.

FIG. 7 is a schematic diagram illustrating a front perspective view of a second example icepack 700, in accordance with aspects herein. In some aspects, the icepack 700 represents any of the icepacks described with respect to the cooling garments systems of FIG. 1, FIG. 2, FIG. 3, and/or FIG. 4. The icepack 700 includes a top or upper portion 708, which includes a first aperture 710. The first aperture 710 is an open space, slit, or hole that is cylindrical in shape in order to receive a shoulder strap (e.g., the shoulder strap 104-1), such that the shoulder strap can fasten to the icepack 700, as described in FIG. 2 for example. In some aspects the upper portion 708 is not configured to be filled with a liquid or substance, but is a panel that is configured to protrude or be exposed outside of a pocket inlet (e.g., the pocket 106-1) so that a wearer can easily place or remove the icepack 700 and/or easily fasten a shoulder strap to the icepack 700 via the first aperture 710. In some aspects, the upper portion 708 is or includes any suitable material, such as foam or any other polymer-based material. In some aspects, the upper portion 708 is made from a different material than the body 712 of the icepack 700.

The body 712 includes flexion areas 716-1, 716-2 (collectively referred to herein as the flexion areas 716) that surround a second aperture 714. Although the icepack 700 illustrates a particular shape, orientation, quantity, and length of flexion areas, apertures, and icepacks themselves, it is understood that this is illustrative only and that any suitable shape, quantity, orientation, and length can exist. For example, in some aspects, the second aperture 714 represents a circular, triangular, rectangular, or square shape, as opposed to diamond-shaped as represented in FIG. 7. In another example, some or each of the flexion areas 716 are circular in shape, as opposed to cylindrical as represented in FIG. 7.

Each of the flexion areas 716 is an area at which a first respective front portion of the icepack 700 and a first respective back portion of the icepack 700 are affixed and/or bonded to each other, as described in more detail below. Accordingly, the flexion areas 716-1 and 716-2 are unable to be filled with a filler substance, such as water. The flexion area 716-1 is cylindrical in shape and extends longitudinally from just inferior to a top edge 712-1 (the horizontal border between the upper portion 708 and a body 712 of the icepack 700) to just above or superior to the second aperture 714. The flexion area 716-2 extends parallel with and is substantially aligned with the flexion area 716-1. The flexion area 716-2 extends longitudinally across a length of the body 712 from just inferior to the second aperture 714 to just above or superior to a bottom edge 712-2 of the body 512.

The second aperture 714 (or any apertures described with reference to an icepack body) is a hole or opening in an icepack body (e.g., the body 712) that extends from a front or face portion of the icepack through a back or rear portion of the icepack. Accordingly, in these aspects, portions of the body 712 can form the borders of the entire second aperture 714 such that there is open space that forms the aperture. For example, a person can see through these apertures and some objects can pass through the apertures (e.g., a finger) in some aspects. FIG. 7 illustrates a diamond-shaped second aperture 714, with vertices or points 714-1 and 714-2 that define the aperture 714. In various aspects the apertures (e.g., second aperture 714) within the bodies of the icepacks are disposed adjacently or next to flexion areas, such as the flexion areas 716. The second aperture 714, in an example aspect, is disposed near the center of the body 512 and in between the flexion areas 716-1 and 716-2. The vertex 714-1 and/or 714-2 may be oriented towards a midline of a cooling garment or wearer of the cooling garment.

Each of the flexion areas 716 and the second aperture 714 allow more flexibility for cooling garments and wearers, as well as allow the icepack 700 to more easily conform to a wearer. For example, the flexion areas 716-1 and 716-2 extend across a portion of the longitudinal length of the body 512. Accordingly, if a wearer performs a horizontal adduction or horizontal abduction movement of the arm (e.g., a throwing motion), this may cause the body 712 to move or rotate in the direction of the movement, which may be substantially perpendicular to the flexion areas 716. Accordingly, the flexion areas 716 may act as an effective axis point or area such that the body 712 of the icepack 700 can more freely move, thereby allowing more unabated range of motion by the wearer and greater contact of the icepack with the wearer, which can reduce discomfort or strain during movement. Likewise, the flexion areas 716 may act as effective joints, such that the body 712 of the icepack 700 can more easily conform to varied contours of a wearer's body, such as a chest region. In another example, if a wearer performs a flexion and extension movement of his or her trunk (e.g., a sit up motion), the second aperture 714 may act as an effective axis point at the vertices 714-1 and 714-2 so that a wearer can more easily flex and extend her trunk while at the same time allow for optimal contact between the body 712 of the icepack 700 and the wearer. Accordingly, in these movements, the second aperture 714 can bend or fold at the vertices 714-1 and 714-2, and the body 712 of the icepack 700 can thus bend or fold at these areas during flexion and extension movements.

In various aspects, the body 712 is made from any suitable material. For example, the body 712 can be made from a thermoplastic-polyurethane material and/or other polymers such as low-density polyethylene, high-density polyethylene, polypropylene, etc. The size of the icepack 700 can also include any suitable length, width, and thickness. For example, in some aspects, the width of the body 712 (defined by a distance along the edge 712-2) is about 10 cm (e.g., plus or minus 5% of 10 cm). In some aspects, the length of the icepack 700 (defined by at least a distance along the edges 712-1 and 712-3) is from about 30 cm to about 36 cm with the upper portion 508 (e.g., plus or minus 5% of 30 cm and 36 cm respectively). In some aspects, the thickness of the body 712 is from about 0.5 cm to about 4 cm (e.g., plus or minus 5% of these values) without a fluid (e.g., water) or other filler substance.

Figure 8:
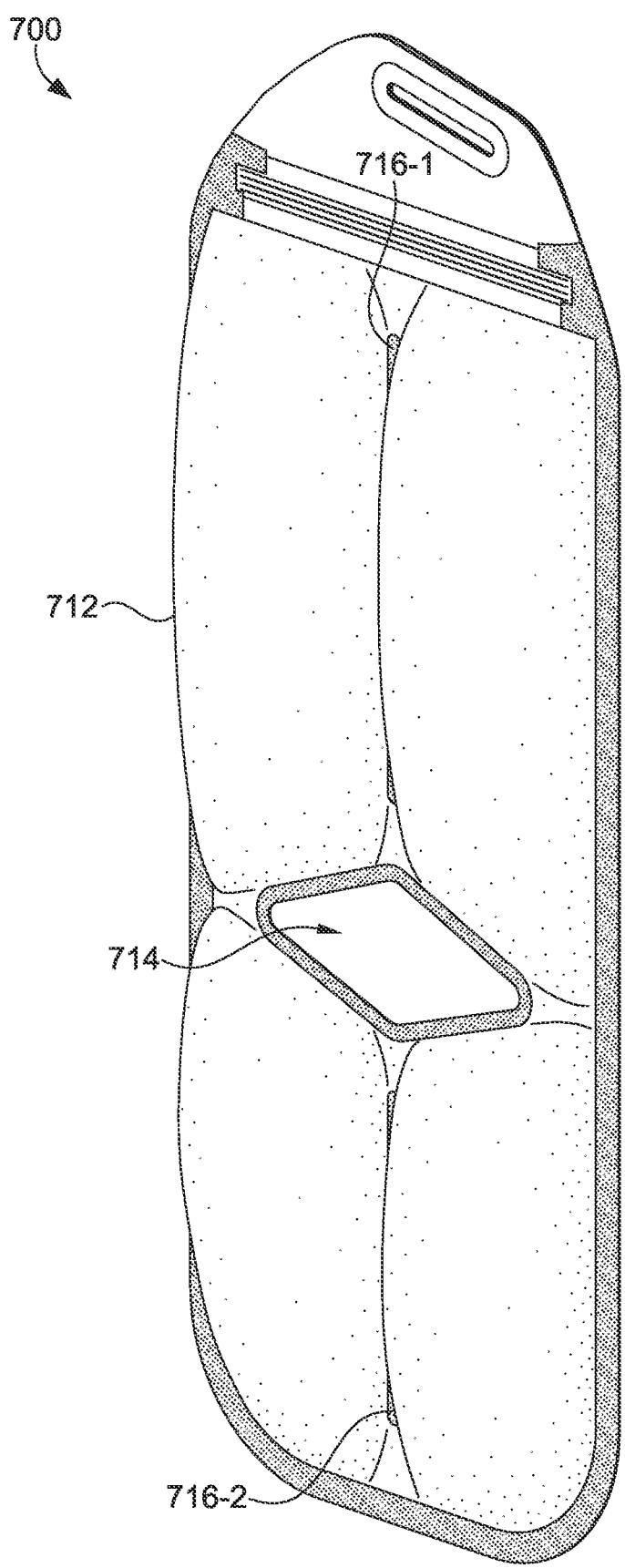
FIG. 8 illustrates a front perspective view of the icepack of FIG. 7, which is filled with a filler substance, in accordance with aspects herein.

As illustrated in FIG. 7, the flexion areas 716 do not extend to any of the edges of the icepack 700. Accordingly, fluid or other substances can surround each portion of each of the flexion areas. For example, the first edge 712-1 of the body 512 may extend across a longitudinal length of the body 712. The second edge 712-2 may extend along a horizontal width from the edge 712-1 to a portion (e.g., a corner) of the edge 712-3. The third edge 712-3 may be parallel with and extend the same distance as the edge 712-1. The fourth edge 712-4 may extend across a horizontal width and represent a line of demarcation between the upper portion 708 and the body 712. The fourth edge 712-4 further represents the top of the body 712. The edge 712-4 may be parallel with the edge 712-2. In an illustrative example, the flexion area 716-1 may extend longitudinally from just inferior the edge 712-4 to just above or superior to an edge of the second aperture 714. Accordingly, the flexion area 716-1 does not extend to the edge 712-4 and to the edge of the second aperture 714. Therefore, for example, the portions 712-5 and 712-6 can be filled with water or another filler substance because the flexion area 716-1 does not extend all the way to the edges. In like manner, the other flexion area 716-2 may also not extend to nearby edges such that a filler substance can entirely surround each side of the flexion areas, as illustrated in FIG. 8. In other aspects, however, flexion areas can abut or extend to one or more edges.

In some aspects, the icepack 700 is formed from two separate layers that are adhered together at certain areas such as around the periphery (e.g., edges 712-1, 712-2, and 712-3), at the flexion areas 716 and/or around the perimeter edge of the second aperture 714.

FIG. 8 illustrates a front perspective view of the icepack 700 of FIG. 7, which is filled with a filler substance (e.g., gel, water, ice, etc.), in accordance with aspects herein. FIG. 8 illustrates what the icepack 700 can appear like when it is filled with a filler substance, such as water. Accordingly, the body 712 of the icepack 700 appears as bulging or expanded at the areas outside of the flexion areas 716-1, 716-2 and the second aperture 714. The flexion areas 716 thus do not bulge or expand upon filling the icepack 700 with a filler substance because the flexion areas 716 are areas where the front and back layers of the icepack 700 are affixed, as described above. The second aperture 714 also does not bulge or expand upon filling the icepack 700 because the body 712 does not continue into this area. As such, water or other filler substances does not fill this space. FIG. 8 also illustrates that the flexion areas 716 and the second aperture 714 can be completely or entirely surrounded by a fluid or other filler substance, such that each area surrounding the second aperture 714 and flexion areas 716 is configured to bulge out or expand in response to filling the icepack 700 with a filler substance.

Figure 9:
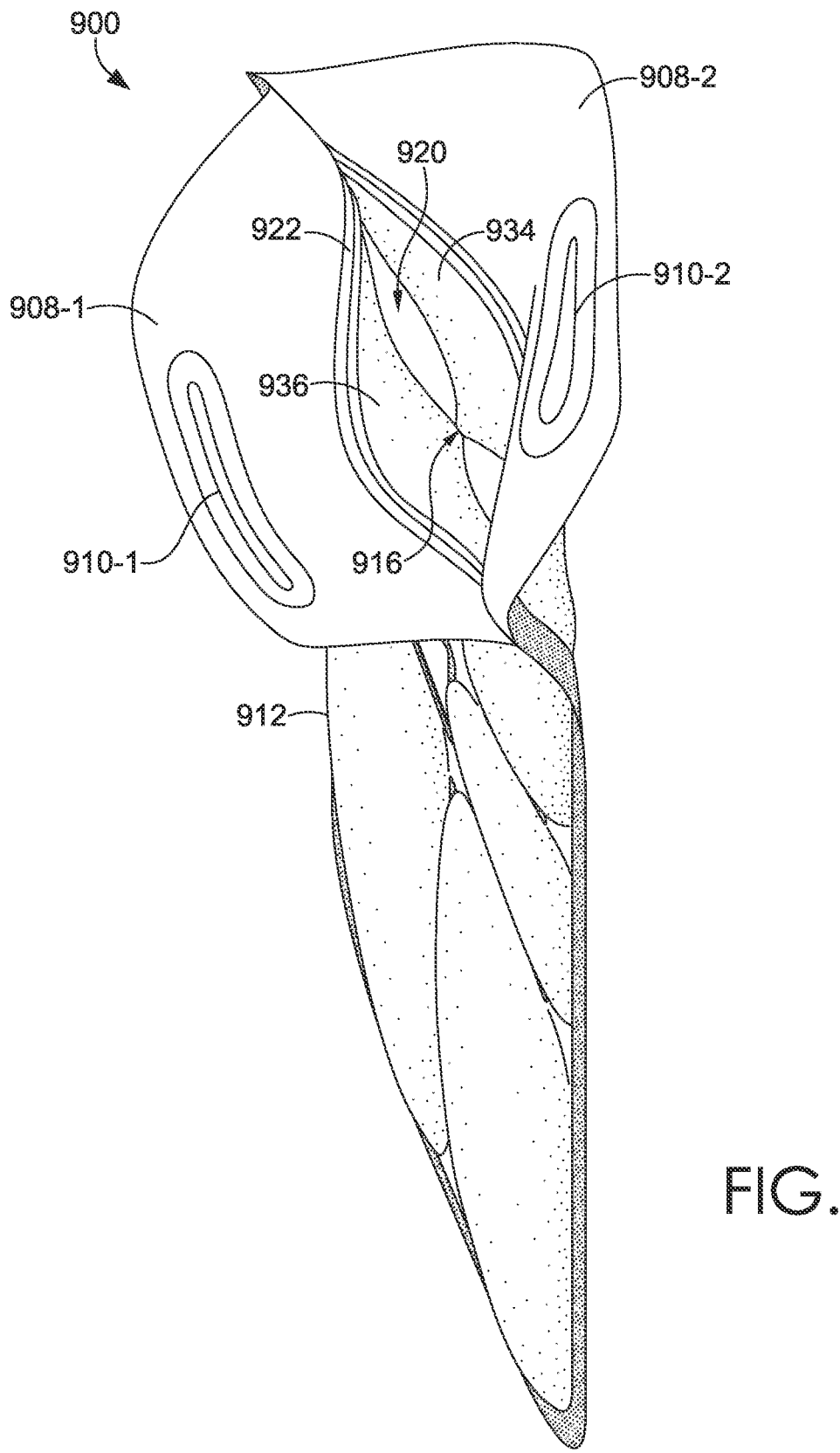
FIG. 9 illustrates a side top view of an opened icepack, in accordance with aspects herein.

FIG. 9 illustrates a side top view of an opened icepack 900, in accordance with aspects herein. In some aspects, the icepack 900 represents a side top view of the icepack 500 icepack 700 of FIGS. 5-8, and/or any icepack described herein, such as with respect to the icepack 108-1. FIG. 9 illustrates how an icepack may appear when a person opens the icepack 900 up to fill it with a filler substance or remove the filler substance, according to certain aspects. At a first time, the icepack 900 may be closed, such that the body 912 remains sealed or otherwise secured. In some aspects, the securing or sealing of the body 912 occurs by a zipper seal 922, which is disposed just superior to an upper portion of the body 912 and inferior to the bottom of upper portions 908-1 and 908-2. The zipper seal 922 includes an interlocking groove and ridge that form a seal when pressed together. Although the zipper seal 922 is described, it is understood that any suitable fastening mechanism or seal can be used to close the body 912, such as permanently bonding the body 912 together. With respect to this aspect, the icepack 900 would be filled with a filler substance prior to sealing.

At the first time (before opening the body 912 or the upper portions 908), the upper portions 908 may appear as one single piece, as illustrated by the upper portion 708 of FIG. 7, for example. However, at a second time (which is subsequent to the first time), a user, such as wearer may open up the icepack 900 by exerting an opposing tension force on the upper portion 908-1 and the upper portion 908-2 causing the two portions to separate from one another. When this separation occurs, the first aperture (such as first aperture 710, as represented in FIG. 7), in certain aspects may appear divided or become two apertures because there are two sides of the icepack (front and back side), as represented by the apertures 910-1 and 910-2 of FIG. 9. The user may then unlock or unzip the zipper seal 922 in order to fill the body 912 with a filler substance by inserting the filler substance into the cavity 920 or bladder opening, which is the inside of the body 912. The user may then, at a third subsequent time, place the groove and ridge portions of the zipper seal 922 together to once again form a seal in order to keep the filler substance within the body 912.

FIG. 9 also illustrates how a flexion area, as described herein, can be formed according to certain aspects. The flexion area 916 illustrates an area at which a first front side 936 and a second back side 934 of the body 912 converge or are affixed to each other to form the flexion area 916. Accordingly, when a user fills the cavity 920 with a filler substance, the filler substance will surround the flexion area 916. In various aspects, the front side 936 and the back side 934 are bonded together in any suitable fashion, such as a permanent adhesive, epoxy adhesives, etc.

The following clauses represent exemplary aspects of concepts contemplated herein. Any one of the following clauses may be combined in a multiple dependent manner to depend from one or more other clauses. Further, any combination of dependent clauses (clauses that explicitly depend from a previous clause) may be combined while staying within the scope of aspects contemplated herein. The following clauses are exemplary in nature and are not limiting.

Clause 1. A cooling garment comprising:
a vest configured to be worn by a wearer;
at least one shoulder strap disposed over a shoulder region of the vest; and
one or more pockets on the vest configured to receive one or more icepacks, the one or more pockets including a stretch material on a front portion of the one or more pockets and the one or more pockets further including a non-stretch material on a back portion of the one or more pockets.

Clause 2. The cooling garment of clause 1, wherein the at least one shoulder strap includes a first end that is configured to be placed through at least one aperture of the one or more icepacks.

Clause 3. The cooling garment of clause 1 or 2 wherein the one or more pockets include a first pocket and a second pocket on the front portion of the vest, wherein the first pocket and the second pocket are configured to receive a first icepack and a second icepack of the one or more icepacks respectively.

Clause 4. The cooling garment of clause 3 or 2, wherein the one or more pockets include a third pocket and a fourth pocket on the back portion of the vest, wherein the third pocket and the fourth pocket are configured to receive a third icepack and a fourth icepack of the one or more icepacks respectively.

Clause 5. The cooling garment of clause 4, 3, 2, or 1 further comprising a first shoulder strap and a second shoulder strap, the first shoulder strap including a first end and a second end, the second shoulder strap including a third end and a fourth end, wherein the first end of the first shoulder strap is configured to fasten to the first icepack, the second end of the first shoulder strap is configured to fasten to the third icepack, and wherein the third end of the second shoulder strap is configured to fasten to the second icepack, the fourth end is configured to fasten to the fourth icepack.

Clause 6. The cooling garment of clause 1, 2, 3, 4, or 5, wherein the stretch material includes a stretch-woven material.

Clause 7. A system comprising:
one or more icepacks that each include at least a first aperture;
a garment that includes one or more pockets configured to receive the one or more icepacks;
at least one shoulder strap disposed over a shoulder region of the garment, the at least one shoulder strap comprising at least a first end, the first end being configured to pass through the first aperture of the one or more icepacks to secure the at least one shoulder strap to the one or more icepacks.

Clause 8. The system of clause 7, wherein at least one of the one or more icepacks include at least one flexion area, the at least one flexion area corresponding to one or more areas at which a first front portion of the at least one of the one or more icepacks and a first back portion of the at least one of the one or more icepacks are affixed to each other, wherein the at least one flexion area is not configured to be filled with a filler substance.

Clause 9. The system of clause 7 or 8, wherein at least one of the one or more icepacks includes a second aperture extending from a front portion of the at least one of the one or more icepacks through a back portion of the at least one of the one or more icepacks.

Clause 10. The system of clause 7, 8, or 9, wherein the one or more pockets including a stretch material on a front portion of the one or more pockets and the one or more pockets further including a non-stretch material on a back portion of the one or more pockets.

Clause 11. The system of clause 7, 8, 9, or 10 wherein at least one of the one or more icepacks includes a second aperture that is triangular shaped, wherein an apex of the second aperture is oriented towards a midline of the garment.

Clause 12. The system of clause 7, 8, 9, or 10 wherein at least one of the one or more icepacks includes a second aperture that is diamond shaped, wherein a vertex of the second aperture is oriented towards a midline of the garment.

Clause 13. The system of clause 7, 8, 9, or 10 wherein at least one of the one or more icepacks includes a plurality of flexion areas that surround a second aperture, wherein the second aperture extends from a front portion of the at least one of the one or more icepacks through a back portion of the at least one of the one or more icepacks, and wherein the second aperture is positioned inferior to the first aperture of the at least one of the one or more icepacks.

Clause 14. The system of clause 7, 8, 9, or 10 wherein the at least one shoulder strap includes a first shoulder strap and a second shoulder strap, and wherein the first shoulder strap is fastened to a first icepack and a second icepack of the one or more icepacks, and wherein the second shoulder strap is fastened to a third icepack and a fourth icepack of the one or more icepacks.

Clause 15. An icepack configured for use with a cooling garment, the icepack comprising:
    at least one flexion area, the at least one flexion area corresponding to one or more areas at which a first front portion of the icepack and a first back portion of the icepack are affixed to each other, wherein the one or more areas are not configured to be filled with a filler substance; and
    one or more apertures disposed adjacently to the at least one flexion area, the one or more apertures extending from a second front portion of the icepack through a second back portion of the icepack.

Clause 16. The icepack of clause 15, further comprising an additional aperture on an upper portion of the icepack that receives a first end of at least one shoulder strap to help secure the icepack.

Clause 17. The icepack of clause 15 or 16, wherein the one or more apertures include a triangular shaped aperture that includes an apex, the apex oriented towards a side edge of the icepack.

Clause 18. The icepack of clause 17 or 16, wherein the at least one flexion area includes a first flexion area oriented parallel to a first side of the triangular shaped aperture, the at least one flexion area further includes a second flexion area oriented parallel to a second side of the triangular shaped aperture.

Clause 19. The icepack of clause 15, 16, 17, or 18, wherein the icepack includes: a first edge, a second edge, a third edge, and a fourth edge, and wherein the at least one flexion area includes a first flexion area that does not extend to: the first edge, the second edge, the third edge, and the fourth edge, and wherein the first flexion area is configured to be entirely surrounded by the filler substance.

Clause 20. The icepack of clause 15, 16, 17, or 18 wherein the one or more apertures include a diamond shaped aperture and the at least one flexion area includes a first flexion area disposed along a longitudinal length of the icepack and superior to a vertex of the diamond shaped aperture.

Aspects of the present disclosure have been described with the intent to be illustrative rather than restrictive. Alternative aspects will become apparent to those skilled in the art that do not depart from its scope. A skilled artisan may develop alternative means of implementing the aforementioned improvements without departing from the scope of the present disclosure.

It will be understood that certain features and sub combinations are of utility and may be employed without reference to other features and sub combinations and are contemplated within the scope of the claims. Not all steps listed in the various figures need be carried out in the specific order described.

What is claimed is:

1. A system comprising:
    an upper-body garment that includes a pocket;
    the pocket comprising a stretch material on a front portion of the pocket and a non-stretch material on a back portion of the pocket;
    a shoulder strap disposed over a shoulder region of the upper-body garment; and
    an icepack configured to be removably positioned in the pocket, the icepack comprising a first aperture, a second aperture, and a plurality of flexion areas that extend away from the first aperture, wherein the shoulder strap is configured to fasten the icepack to the upper-body garment through the second aperture.

2. The system of claim 1, wherein the non-stretch material on the back portion of the pocket comprises one or more non-elastomeric yarns.

3. The system of claim 1, wherein the stretch material on the front portion of the pocket comprises a stretch-woven material.

4. The system of claim 1, wherein the upper-body garment includes an inner layer that forms the back portion of the pocket.

5. The system of claim 1, wherein the front portion of the pocket includes a lower margin, which comprises the non-stretch material of the back portion of the pocket.

6. The system of claim 1, wherein a first end of the shoulder strap comprises a male end of a connecting element and a female end of the connecting element, the male end and the female end being configured to couple to form a loop, wherein the icepack extends from the loop.

7. The system of claim 6, wherein the icepack comprises a width of about 10 cm and a length of about 30 cm to about 36 cm.

8. The system of claim 1, wherein the shoulder strap is a first shoulder strap, the system further comprising a second shoulder strap, wherein the shoulder strap is fastened to the icepack and the second shoulder strap is fastened to a second icepack.

9. An upper-body cooling garment system comprising:
    an upper-body garment comprising a pocket; and
    one or more icepacks, each of the one or more icepacks comprising a first aperture, a plurality of flexion areas that extend away from the first aperture, and a second aperture, wherein the plurality of flexion areas extending away from the first aperture are configured to allow the icepack to conform to a wearer's body when the upper-body cooling garment system is worn;

wherein the pocket is configure to receive a first icepack of the one or more icepacks; and a shoulder strap disposed over a shoulder region of the upper-body garment and configured to secure to the first icepack via the second aperture.

10. The upper-body cooling garment system of claim 9, wherein the pocket comprises a stretch material formed using one or more elastomeric yarns.

11. The upper-body cooling garment system of claim 9, wherein: the pocket is on a front portion of the upper-body garment; and the upper-body garment further comprises an additional pocket on a back portion of the upper-body garment.

12. The upper-body cooling garment system of claim 9, wherein an outer portion of the pocket includes a lower margin, which comprises a non-stretch material of an inner portion of the pocket.

13. The upper-body cooling garment system of claim 9, further comprising a slider mechanism forming an edge of the pocket.

14. The upper-body cooling garment system of claim 9 further comprising, a second pocket configured to receive a second icepack of the one or more icepacks, the second icepack; and a second shoulder strap configured to secure to the second icepack via the second aperture of the second icepack.

* * * * *

UNITED STATES PATENT AND TRADEMARK OFFICE
CERTIFICATE OF CORRECTION

| | | |
|---|---|---|
| PATENT NO. | : 12,408,710 B2 | Page 1 of 1 |
| APPLICATION NO. | : 17/873949 | |
| DATED | : September 9, 2025 | |
| INVENTOR(S) | : Baron C. Brandt and Kevin C. Sze | |

It is certified that error appears in the above-identified patent and that said Letters Patent is hereby corrected as shown below:

In the Specification

Under Column 1, Line 6, "No. 17,873,949 and" should read --No. 17/873,949 and--.

In the Claims

Under Column 17, Line 28, "icepack; and" should read --icepack and--.

Signed and Sealed this
Twenty-third Day of December, 2025

John A. Squires
*Director of the United States Patent and Trademark Office*